(12) United States Patent
Chang et al.

(10) Patent No.: US 11,583,638 B2
(45) Date of Patent: Feb. 21, 2023

(54) INFUSION TUBE ASSEMBLY, INFUSION DEVICE, AND INFUSION METHOD

(71) Applicants: Inventec Appliances (Pudong) Corporation, Shanghai (CN); Inventec Appliances Corp., New Taipei (TW); Inventec Appliances (Shanghai) Co., Ltd., Shanghai (CN)

(72) Inventors: Wen-Fong Chang, New Taipei (TW); Yen-Hsiang Hsiung, New Taipei (TW); Chia-Yao Chang, New Taipei (TW)

(73) Assignees: Inventec Appliances (Pudong) Corporation, Shanghai (CN); Inventec Appliances Corp., New Taipei (TW); Inventec Appliances (Shanghai) Co., Ltd., Shanghai (CN)

( * ) Notice: Subject to any disclaimer, the term of this patent is extended or adjusted under 35 U.S.C. 154(b) by 863 days.

(21) Appl. No.: 16/420,176

(22) Filed: May 23, 2019

(65) Prior Publication Data

US 2020/0069888 A1 Mar. 5, 2020

Related U.S. Application Data

(60) Provisional application No. 62/723,501, filed on Aug. 28, 2018.

(51) Int. Cl.
*A61M 5/36* (2006.01)
*A61M 1/36* (2006.01)

(52) U.S. Cl.
CPC ......... *A61M 5/365* (2013.01); *A61M 1/3626* (2013.01); *A61M 1/3643* (2013.01)

(58) Field of Classification Search
CPC .......... A61M 5/36; A61M 5/365; A61M 5/38; A61M 5/40; A61M 1/3626; A61M 1/3627; A61M 1/3644
See application file for complete search history.

(56) References Cited

U.S. PATENT DOCUMENTS

| 3,650,093 A | * | 3/1972 | Rosenberg | ............ A61M 5/165 96/219 |
| 2006/0195045 A1 | * | 8/2006 | Gable | .................. A61B 5/1427 600/583 |

(Continued)

FOREIGN PATENT DOCUMENTS

| CN | 1561237 A | 1/2005 |
| CN | 101563121 A | 10/2009 |

(Continued)

*Primary Examiner* — Philip R Wiest
(74) *Attorney, Agent, or Firm* — CKC & Partners Co., LLC (57) ABSTRACT

An infusion device includes an infusion pump and an infusion tube assembly. The infusion tube assembly includes a first tube body connected to the infusion pump, a tube joint structure having first, second and third tube joints, a second tube body, and a clamping device on the second tube body. The clamping device is to clamp the second tube body. An infusion method includes instructing the infusion pump to perform an infusion operation. When bubbles are detected in a liquid in the infusion tube assembly, the infusion pump is instructed to stop the infusion operation and a bubble alarm is generated. After the infusion pump stops the infusion operation, it is determined whether a pressure of the liquid first drops to a first pressure value and then rises to a second pressure value. If yes, a rinsing operation is performed.

5 Claims, 5 Drawing Sheets

(56) References Cited

U.S. PATENT DOCUMENTS

| | | | |
|---|---|---|---|
| 2009/0143726 | A1 | 6/2009 | Bouton et al. |
| 2010/0262078 | A1* | 10/2010 | Blomquist ........ A61M 5/16831 73/40 |
| 2012/0172800 | A1* | 7/2012 | Dudar .................... A61M 5/38 604/123 |
| 2019/0054271 | A1* | 2/2019 | Tsubouchi ....... A61B 5/150366 |

FOREIGN PATENT DOCUMENTS

| | | |
|---|---|---|
| CN | 203829412 U | 9/2014 |
| CN | 105338914 A | 2/2016 |
| CN | 205948436 U | 2/2017 |
| WO | 2014149013 A2 | 9/2014 |

\* cited by examiner

INFUSION TUBE ASSEMBLY, INFUSION DEVICE, AND INFUSION METHOD

CROSS-REFERENCE TO RELATED APPLICATION

This application claims priority to U.S. Provisional Application Ser. No. 62/723,501, filed Aug. 28, 2018, which is herein incorporated by reference in its entirety.

BACKGROUND

Technical Field

The present disclosure relates to an infusion tube assembly, an infusion device, and an infusion method, and more particularly to the infusion tube assembly, the infusion device, and the infusion method which may perform removal of bubbles.

Description of Related Art

In a medical treatment, when infusion is required for a patient, an infusion device including an infusion pump and an infusion tube is used to deliver liquid medicine to the patient's vein. However, during the delivery of the liquid medicine, bubbles may enter the infusion tube, and thus the bubbles need to be removed, so as to prevent the bubbles from entering the patient's body with the liquid medicine.

The clinical practice for removing the bubbles generally has to remove the infusion tube from the infusion pump and discharge some of the liquid medicine so as to remove the bubbles together with the medicine liquid. However, this method may not only cause inconvenience to nursing staffs but also waste liquid medicine during the removal of the bubbles. Therefore, how to improve the removal of the bubbles in the infusion tube is an important issue currently.

SUMMARY

According to one embodiment of the present disclosure, an infusion assembly is applied to an infusion pump. The infusion tube assembly includes a first tube body, a tube joint structure, a second tube body, and a clamping device. The first tube body is configured to be connected to the infusion pump. The tube joint structure has a first tube joint, a second tube joint, and a third tube joint. The first tube joint is connected to one end of the first tube body. One end of the second tube body is connected to the second tube joint. The clamping device is disposed on the second tube body and is configured to clamp the second tube body.

According to some embodiments of the present disclosure, the infusion tube assembly further includes a liquid container engaged to the third tube joint.

According to another embodiment of the present disclosure, an infusion device includes an infusion pump, a first tube body, a tube joint structure, a second tube body, and a clamping device. The first tube body is configured to be connected to the infusion pump. The tube joint structure has a first tube joint, a second tube joint, and a third tube joint. The first tube joint is connected to one end of the first tube body. One end of the second tube body is connected to the second tube joint. The clamping device is disposed on the second tube body and is configured to clamp the second tube body.

According to some embodiments of the present disclosure, the infusion device further includes a liquid container engaged to the third tube joint.

According to some embodiments of the present disclosure, the tube joint structure is Y-shaped.

According to some embodiments of the present disclosure, an angle between the first tube joint and the third tube joint is an acute angle.

According to some embodiments of the present disclosure, an angle between the first tube joint and the second tube joint is an obtuse angle.

According to another embodiment of the present disclosure, an infusion method is applied to an infusion pump connected to an infusion tube assembly, in which the infusion tube assembly includes a first tube body, a tube joint structure connected to the first tube body, and a second tube body connected to the tube joint structure. The infusion method includes the following steps. The infusion pump is instructed to perform an infusion operation. When bubbles are detected in a liquid delivered in the infusion tube assembly, the infusion pump is instructed to stop the infusion operation and a bubble alarm is generated. After the infusion pump stops the infusion operation, the method determines whether a pressure of the liquid drops to a first pressure value. If the pressure of the liquid drops to the first pressure value, the method further determines whether the pressure of the liquid rises to a second pressure value. If the pressure of the liquid rises to the second pressure value, a rinsing operation is performed.

According to some embodiments of the present disclosure, the method further includes before determining whether the pressure of the liquid drops to the first pressure value, generating a prompt signal for clamping the second tube body.

According to some embodiments of the present disclosure, the method further includes before determining whether the pressure of the liquid rises to the second pressure value, generating a first prompt signal for installing a liquid container at the tube joint structure.

According to some embodiments of the present disclosure, the method further includes after no bubbles are detected during the rinsing operation, generating a second prompt signal for removing the liquid container and opening the second tube body.

According to some embodiments of the present disclosure, the method further includes determining whether the bubbles are detected while the rinsing operation is performed. If no bubbles are detected during the rinsing operation, the infusion pump is instructed to continuously perform the infusion operation for a predetermined period of time and then stop the infusion.

In summary, the disclosure provides the infusion tube assembly, the infusion device, and the infusion method. By using the infusion structure and the infusion method, the bubbles in the infusion tube can be effectively removed with a simple. The removal of the bubbles may be performed without taking out the infusion tube. Furthermore, since the liquid container is connected to the tube joint structure, the loss of the liquid medicine can be reduced during the removal of the bubbles. In addition to reducing the loss of the liquid medicine, the liquid medicine flowing into the liquid container may be recycled and reused.

It is to be understood that both the foregoing general description and the following detailed description are by examples, and are intended to provide further explanation of the disclosure as claimed.

BRIEF DESCRIPTION OF THE DRAWINGS

The disclosure can be more fully understood by reading the following detailed description of the embodiment, with reference made to the accompanying drawings as follows.

DETAILED DESCRIPTION

Reference will now be made in detail to the present embodiments of the disclosure, examples of which are illustrated in the accompanying drawings. Wherever possible, the same reference numbers are used in the drawings and the description to refer to the same or like parts.

Figure 1:
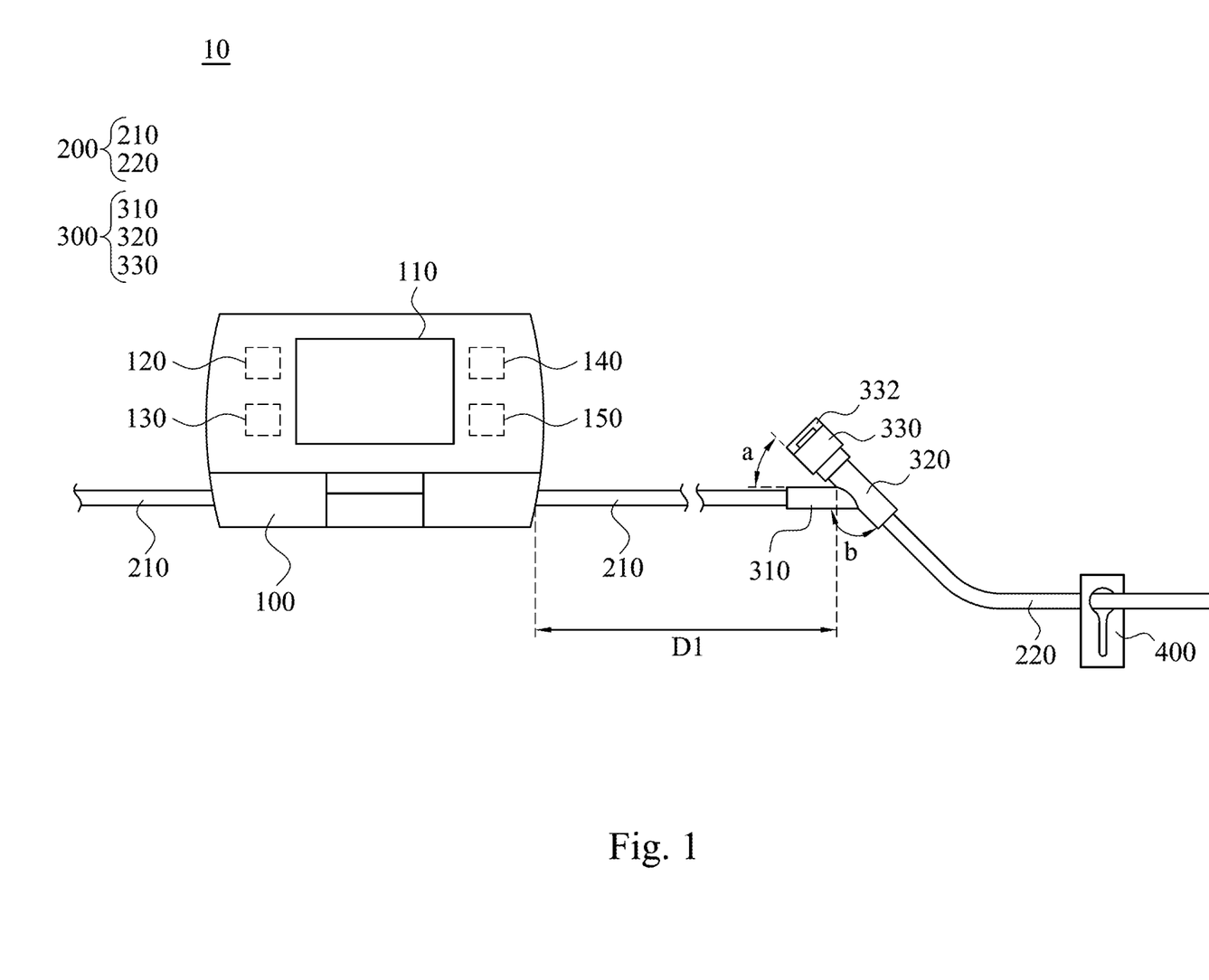
FIG. 1 is a schematic view showing an infusion tube assembly and an infusion device in one operation state in accordance with one embodiment of the present disclosure.
Figure 2:
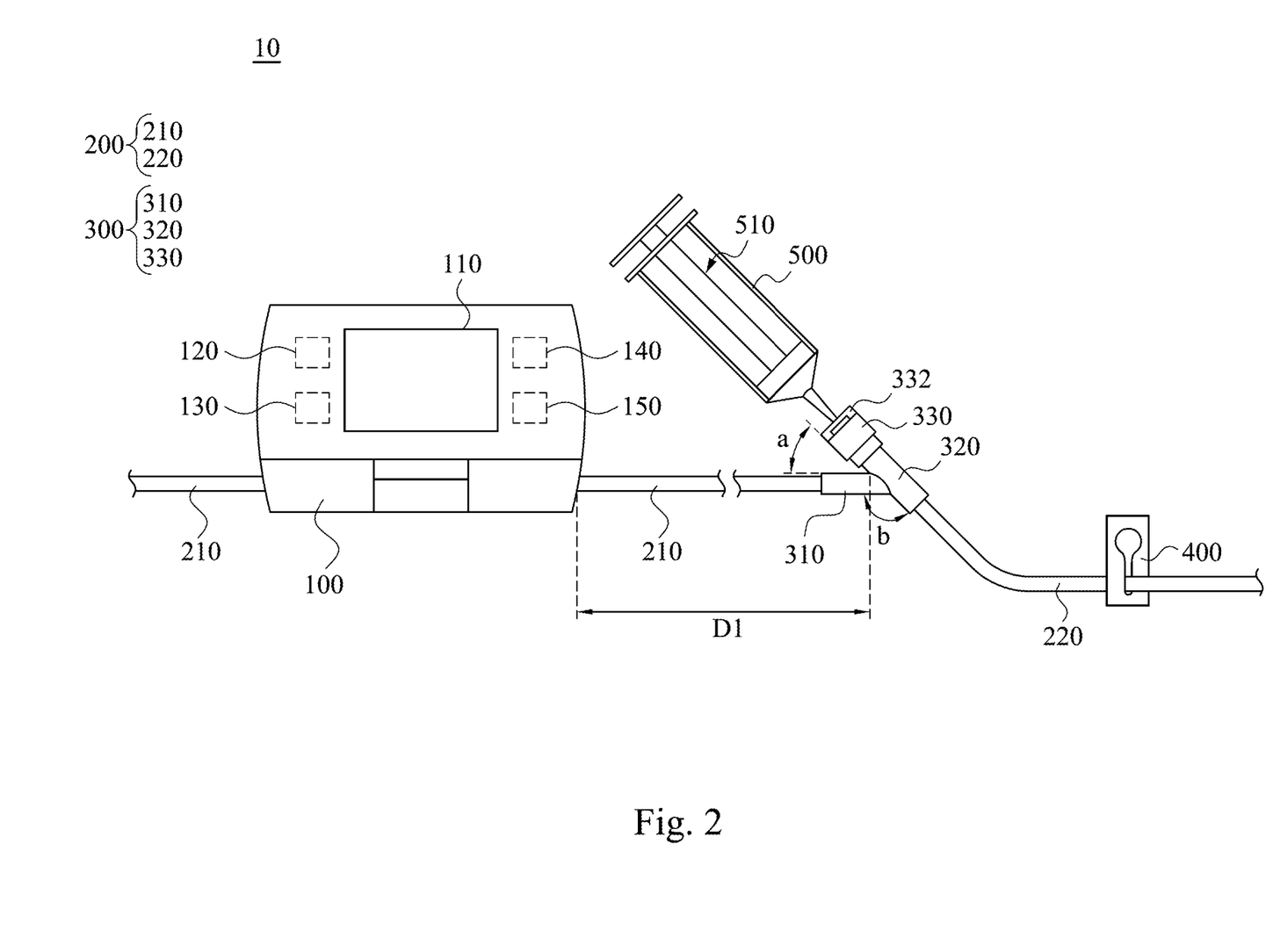
FIG. 2 is a schematic view showing the infusion tube assembly and the infusion device in another operation state in accordance with one embodiment of the present disclosure.
Figure 3:
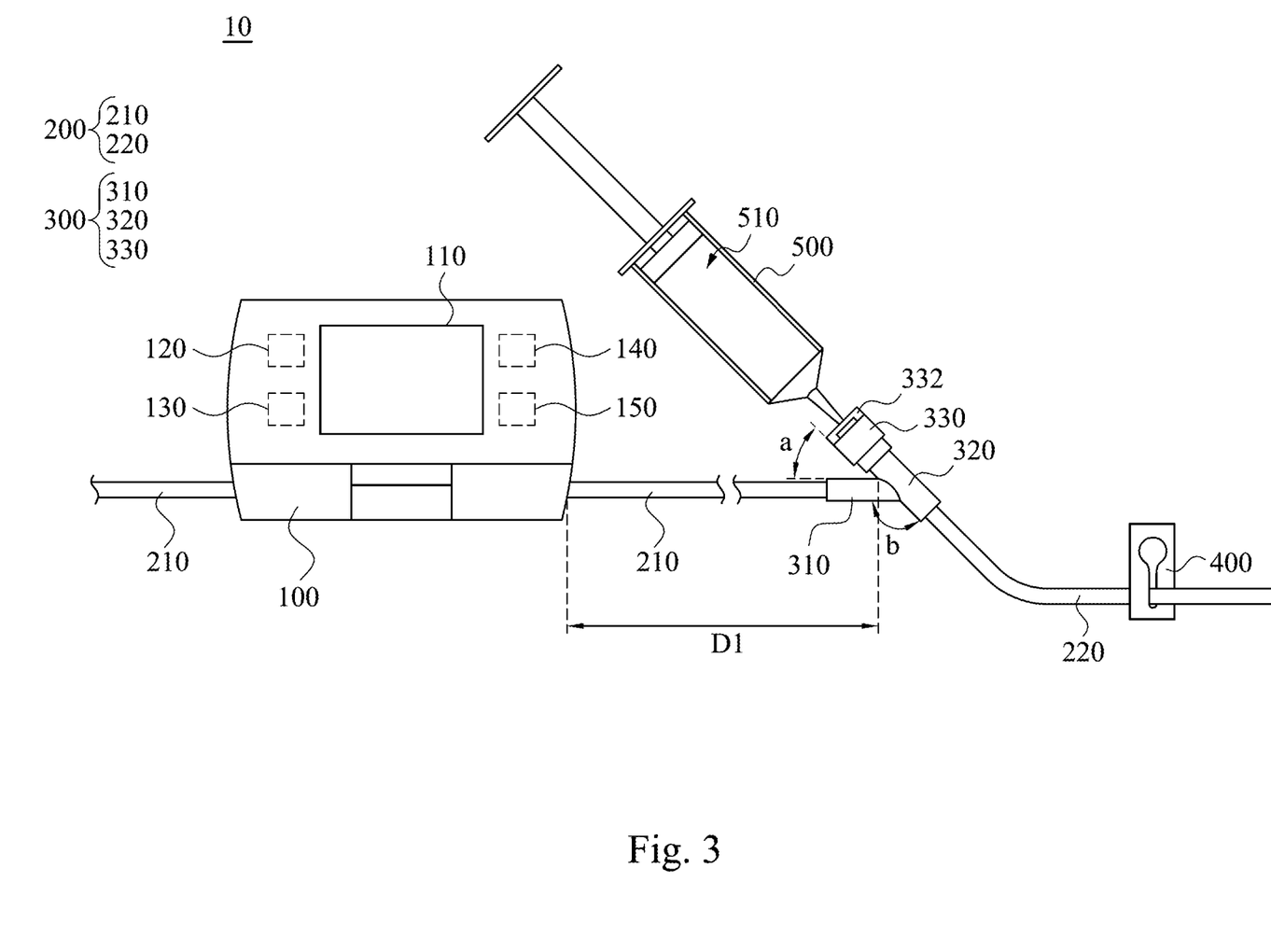
FIG. 3 is a schematic view showing the infusion tube assembly and the infusion device in another operation state in accordance with one embodiment of the present disclosure.

FIG. 1 to FIG. 3 are schematic views showing an infusion tube assembly and an infusion device 10 in different operation states in accordance with one embodiment of the present disclosure. Referring to FIG. 1, in the present embodiment, the infusion device 10 includes an infusion pump 100 and the infusion tube assembly applied to the infusion pump 100. The infusion pump 100 is configured to deliver liquid medicine to a patient's body by using the infusion tube assembly in a controlling manner. The infusion pump 100 has a display screen 110, a controller 120, a pressure sensor 130, a bubble sensor 140, and an alarm 150. The display screen 110 is used to display different operating states and prompt signals of the infusion pump 100. The controller 120 is electrically connected to the display screen 110, the pressure sensor 130, the bubble sensor 140 and the alarm 150, so as to control the operation of the infusion pump 100, and display the operation state and the prompt signal on the display screen 110. The pressure sensor 130 is used to measure a pressure of a liquid in the infusion tube 200. The bubble sensor 140 is used to detect whether the liquid in the infusion tube 200 contains bubbles. When the bubbles are detected, a bubble alarm is issued through the alarm 150. In some embodiments, the infusion pump 100 is a push pump, a cylindrical pump, or a digital peristaltic pump, and has two types of power including kinetic power and mechanical power.

As shown in FIG. 1, the infusion tube assembly includes the infusion tube 200 and a tube joint structure 300. The infusion tube 200 includes a first tube body 210 and a second tube body 220. The first tube body 210 is partially disposed in and connected to the infusion pump 100. One end of the first tube body 210 is connected to a vial (not shown), and the other end of the first tube body 210 is connected to the tube joint structure 300. In the present embodiment, the tube joint structure 300 has a first tube joint 310, a second tube joint 320 and a third tube joint 330. The first tube joint 310 is connected to the first tube body 210 relative to one end of the infusion pump 100. One end of the second tube body 220 is connected to the second tube joint 320. In other words, the liquid in the first tube body 210 is pushed by the infusion pump 100 to flow through the first tube joint 310, the second tube joint 320, and the second tube body 220, and then flows into the body of the patient.

The tube joint structure 300 is disposed at a position which is a distance D1 away from the end of the infusion pump 100. For example, one side of the infusion tube 200 with the liquid flowing to the infusion pump 100 may be defined as an upstream, while the other side of the infusion tube 200 with the liquid leaving the infusion pump 100 may be defined as a downstream. The tube joint structure 300 is disposed at the downstream of the infusion pump 100 which is the distance D1 away from the end of the infusion pump 100. In some embodiments, the distance D1 is in a range from about 5 cm to about 15 cm. When the distance D1 is greater than 15 cm, it takes more time to remove the bubbles, which is not beneficial for the infusion operation to be performed. When the distance D1 is less than 5 cm, the installation of a liquid container (the liquid container 500 will be discussed below) at the tube joint structure 300 may likely to interfere with the infusion pump 100, resulting in operational inconvenience. The tube joint structure 300 has a stopping element 332 which is disposed on the third tube joint 330 of the tube joint structure 300. When the liquid flows from the first tube body 210 into the second tube body 220, the stopping element 332 is used to ensure that the liquid does not flow out of the third tube joint 330. In some embodiments, the tube joint structure 300 is Y-shaped. In some embodiments, an angle a is formed between the first tube joint 310 and the third tube joint 330, while an angle b is formed between the first tube joint 310 and the second tube joint 320, and the angle a is smaller than the angle b. For example, the angle a between the first tube joint 310 and the third tube joint 330 is an acute angle less than 90 degrees, while the angle b between the first tube joint 310 and the second tube joint 320 is an obtuse angle greater than 90 degrees. Since the angle b between the first tube joint 310 and the second tube joint 320 has the aforementioned relationship, it is beneficial for the liquid to smoothly flow from the first tube body 210 into the second tube body 220.

In some embodiments, the clamping device 400 is disposed on the second tube body 220 and is configured to clamp the second tube body 220. In the present embodiment, the clamping device 400 may be a slide clamp, but the invention is not limited thereto. In other embodiments, the clamping device 400 may be a roller clamp or another suitable device. A user may open the clamping device 400 to allow the liquid in the second tube body 220 to flow into the patient's body. As shown in FIG. 1, when the clamping device 400 is in an open state, the liquid in the second tube body 220 may flow through the clamping device 400, thereby allowing the liquid to be delivered to the patient. In contrast, if the clamping device 400 is in a closed state, the liquid in the second tube body 220 cannot flow through the clamping device 400, that is, the liquid cannot be continuously delivered to the patient.

Referring to FIG. 2, FIG. 2 is a schematic view showing the infusion tube assembly and the infusion device 10 in another operation status in accordance with one embodiment of the present disclosure. As shown in FIG. 2, the clamping device 400 is in a closed state, such that liquid in the second tube body 220 cannot flow through the clamping device 400. Thereafter, the infusion device 10 may further include a liquid container 500 configured to accommodate the liquid flowing out of the third tube joint 330. The liquid container 500 is detachably connected to the third tube joint 330 of the tube joint structure 300 and has a variable volume 510, but the invention is not limited thereto. For example, the liquid container 500 may be a container having an opening, and the opening is closed with a waterproof ventilation membrane and the opening may allow the liquid to flow out of the third tube joint 330. The liquid container 500 may also be an empty syringe having a variable volume 510 to accommodate the liquid flowing out of the third tube joint 330. In some embodiments, the volume of the liquid container 500 is selected to be related to the distance D1. For example, when the distance D1 is 5 cm, the discharged bubble-containing volume is about 1.807 mL, and thus the volume of the liquid container 500 needs to be greater than 1.807 mL. When the distance D1 is 10 cm, the discharged bubble-containing volume is about 2.16 mL, and thus the volume of the liquid container 500 needs to be greater than 2.16 mL. When the distance D1 is 15 cm, the discharged bubble-containing volume is about 2.513 mL, and thus the volume of the liquid container 500 needs to be greater than 2.513 mL.

Referring to FIG. 3, FIG. 3 is a schematic view showing the infusion tube assembly and the infusion device 10 in another operation status in accordance with one embodiment of the present disclosure. As shown in FIG. 3, when the clamping device 400 is in the closed state, the liquid in the second tube body 220 cannot continue to pass through the clamping device 400 and flows to the third tube joint 330 instead. At this time, the liquid flowing out of the third tube joint 330 passes through the stopping element 332 on the third tube joint 330 and then flows into the liquid container 500. In the present embodiment, the liquid container 500 has a variable volume 510 which may collect the liquid flowing out through the third tube joint 330, and the liquid may be recycled and reused without wasting the liquid medicine.

Figure 4:
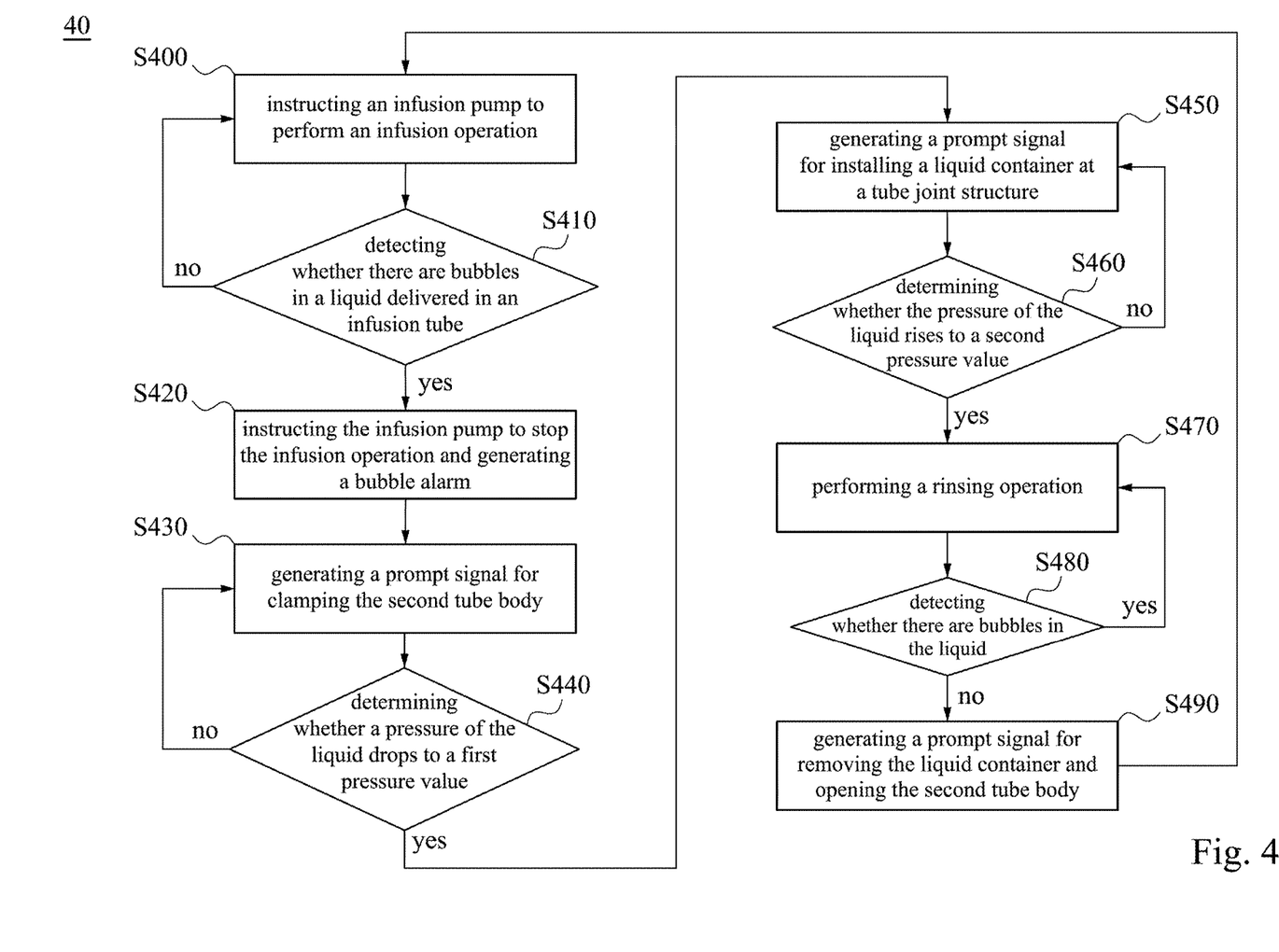
FIG. 4 is a flow chart showing an infusion method in accordance with one embodiment of the present disclosure.
Figure 5:
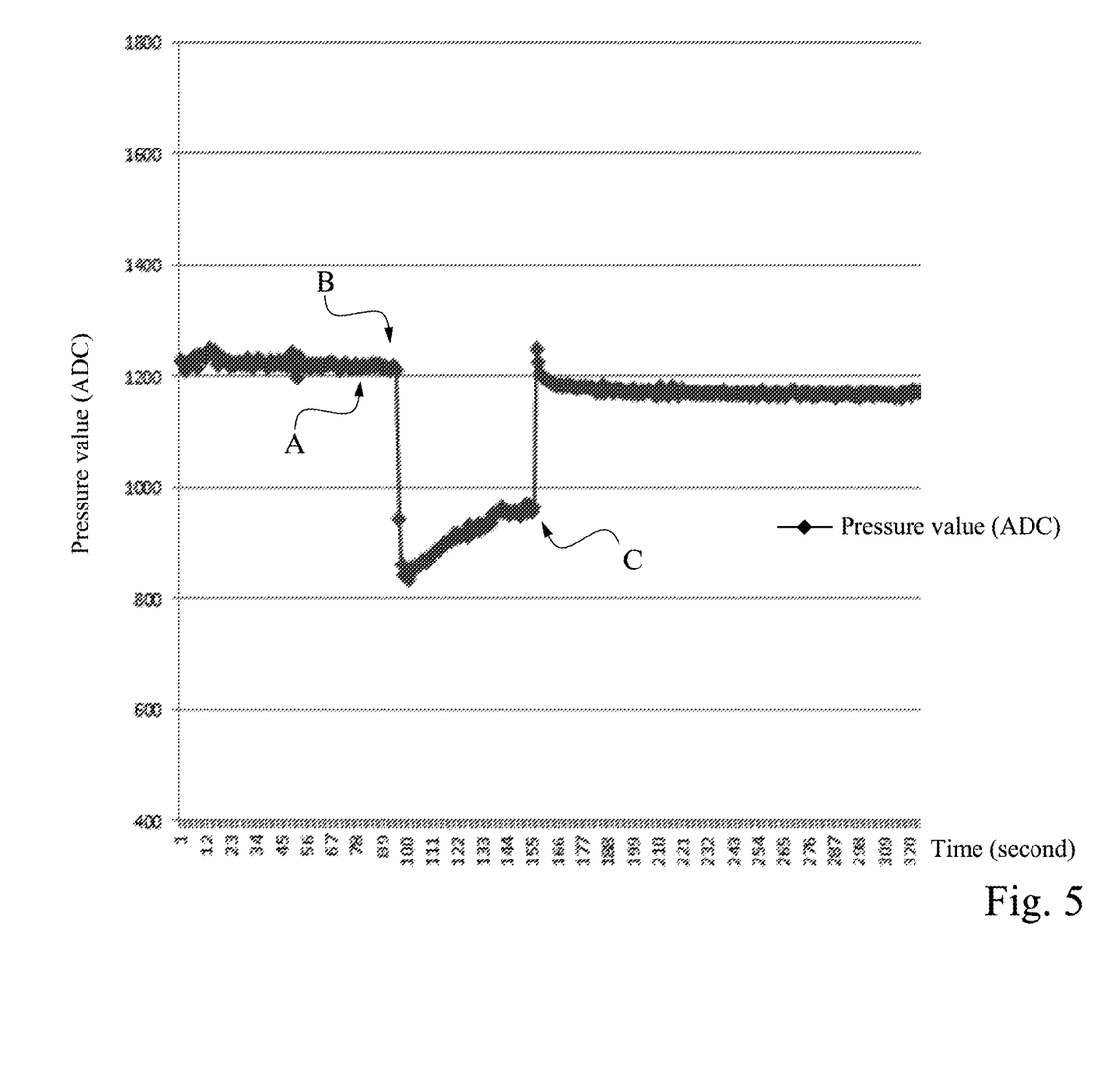
FIG. 5 is a chart showing pressure variation of the liquid in the infusion tube when the infusion method of FIG. 4 is performed.

Referring to FIGS. 4 and 5, FIG. 4 is a flow chart showing an infusion method 40 in accordance with one embodiment of the present disclosure, and FIG. 5 is a chart showing pressure variation of the liquid in the infusion tube when the infusion method 40 of FIG. 4 is performed. The infusion method 40 is described below in conjunction with the infusion device 10 shown in FIG. 1 to FIG. 3. The infusion method 40 includes operations S400 to S490. In other words, the infusion method 40 may be applied to an infusion pump 100 which is connected to an infusion tube assembly, in which the infusion tube assembly includes a first tube body 210, a tube joint structure 300 connected to the first tube body 210, and a second tube body 220 connected to the tube joint structure 300. In addition to operations S400 to S490 shown in FIG. 4, additional operations can be provided before, during, and after the infusion method 40, and some operations described herein can be replaced, eliminated, or moved around to achieve additional embodiments without departing from the scope of the present disclosure.

Operations S400 to S490 are described below. At operation S400, an infusion pump 100 is instructed to perform an infusion operation. For example, the controller 120 of the infusion pump 100 may control the infusion pump 100 to perform the infusion operation. The first tube body 210 is partially disposed in and connected to the infusion pump 100. One end of the first tube body 210 is connected to the vial (not shown), and the other end is connected to the tube joint structure 300. The liquid flows from the first tube body 210 to the tube joint structure 300 and is delivered to the patient's body through the second tube body 220.

Operation S410 is performed to detect whether there are bubbles in the liquid delivered in the infusion tube 200 of the infusion tube assembly. For example, the bubble sensor 140 of the infusion pump 100 may detect whether there are bubbles in the liquid. If there are no bubbles in the liquid, the infusion pump 100 continuously performs the infusion operation. If there are bubbles in the liquid, operation S420 is performed.

At operation S420, the infusion pump 100 is instructed to stop the infusion operation and a bubble alarm is generated. For example, the aforementioned controller 120 may generate the bubble alarm at this time. Furthermore, the controller 120 may display the bubble alarm on the display screen 110, or may further send out an alarm sound through the alarm 150 to clearly remind the user that bubbles appear in the liquid. Referring to FIG. 5, in a period from the infusion pump 100 performing the infusion operation through the bubble sensor 140 in the infusion pump 100 detecting the bubbles, to the infusion pump 100 stopping the infusion operation and generating the bubble alarm, the pressure of the liquid is maintained at a position A and has no significant changes. In the present embodiment, the pressure of the liquid is converted by an analog-to-digital converter (ADC). Because different converters have different initial values with the pressure sensor 130, subsequent measured ADC values fall within a range of values. For example, as shown in FIG. 5, the ADC value of the pressure of the liquid is about 1220 during the period from the start of the infusion operation to about 85 seconds at which the infusion operation is stopped and the bubble alarm is generated. In some embodiments, the ADC value changes are the pressure differences of the pressure sensor 130, and the voltage values output by the pressure sensor 130 is at a millivolt (mV) level. As a result, the voltage value needs to be amplified by an amplifier, so as to convert the analog voltage signal to a software-determinable digital ADC value. For example, in the present embodiment, the calculation of the ADC value is obtained by the following equation (1), in which the voltage V in the equation (1) is the voltage output through the amplifier.

$$ADC \text{ value} = \frac{V \times 4096}{3300}. \tag{1}$$

At operation S430, a prompt signal is generated for clamping the second tube body 220. For example, the controller 120 may generate the prompt signal at this time and display the prompt signal on the display screen 110. As shown in FIG. 2, after the prompt signal is generated, the effect of clamping the second tube body 220 may be achieved by the user's manual operation or automatically closing the clamping device 400 by machine, but the disclosure is not limited thereto. The effect of clamping the second tube body 220 may be achieved by other suitable methods. As a result, the liquid will stop flowing in the second tube body 220 without flowing into the patient's body.

Operation S440 is performed to determine whether the pressure of the liquid drops to a first pressure value. As shown by point B of FIG. 5, when the second tube body 220 is clamped, the pressure of the liquid drops to the first pressure value. For example, the ADC value of the pressure of the liquid drops from the initial pressure of the liquid, e.g., about 1220, to the first pressure value, e.g., about 870, and the initial pressure of the liquid drops about 350 to the first pressure value. In some embodiments, the reference value of the first pressure value may be different due to a different infusion pump 100 selected by the user. In general, the ADC value between the initial pressure of the liquid and the first pressure value may differ in a range between about 250 and about 450. Referring back to operation S440, after the prompt signal for clamping the second tube body 220 is generated, the controller 120 may detect whether the pressure of the liquid drops to the first pressure value, thereby determining whether the second tube body 220 is already clamped to prevent the liquid from flowing into the patient's body with bubbles in subsequent operations of removing bubbles. If the pressure of the liquid drops to the first pressure value, the controller 120 determines that the second tube body 220 is already clamped, and proceeds to operation S450. If the pressure of the liquid does not drop to the first pressure value, the controller 120 determines that the second tube body 220 is not clamped, and returns to operation S430 to generate and display the prompt signal for clamping the second tube body 220 on the display screen 110 to remind the user to clamp the second tube body 220.

At operation S450, after the pressure of the liquid drops to the first pressure value, a prompt signal for installing the liquid container 500 at the tube joint structure 300 is generated. For example, the controller 120 may generate the prompt signal at this time and display the prompt signal on the display screen 110. As shown in FIG. 2, after the prompt signal is generated, the effect of installing the liquid container 500 at the tube joint structure 300 may be achieved by the user's manual operation or by machine automatically. In the greater detail, the tube joint structure 300 may include a first tube joint 310 connected to the first tube body 210, a second tube joint 320 connected to the second tube body 220, and a third tube joint 330. The liquid container 500 is configured to be installed at the third tube joint 330. In some embodiments, when the liquid container 500 is installed at the third tube joint 330, the liquid may pass through the stopping element 332 on the third tube joint 330 and flow into the liquid container 500.

Operation S460 is performed to determine whether the pressure of the liquid rises to a second pressure value is performed. As shown by point C in FIG. 5, when the liquid container 500 is installed at the tube joint structure 300, the pressure of the liquid rises to the second pressure value. In other words, the second pressure value is greater than the first pressure value. For example, the pressure of the liquid may rise from the first pressure value, e.g., about 870, to the second pressure value, e.g., about 1200, with a difference between the first pressure value and the second pressure value, e.g., about 330. In some embodiments, the reference values of the first pressure value and the second pressure value may be different due to the different infusion pumps 100 selected by the user. In general, the ADC value between the first pressure value and the second pressure value may differ in a range between about 250 and about 450. Referring back to operation S460, after the prompt signal for installing the liquid container 500 at the tube joint structure 300 is generated, the controller 120 may detect whether the pressure of the liquid rises to the second pressure value, thereby determining whether the liquid container 500 is already installed at the tube joint structure 300. If the pressure of the liquid rises to the second pressure value, the controller 120 determines that the liquid container 500 is already installed at the tube joint structure 300, and proceeds to operation S470. If the pressure of the liquid does not rise to the second pressure value, the controller 120 determines that the liquid container 500 is not installed at the tube joint structure 300, and returns to operation S450 to generate and display the prompt signal for installing the liquid container 500 at the tube joint structure 300 on the display screen 110 to remind the user to install the liquid container 500 at the tube joint structure 300.

At operation S470, a rinsing operation is performed. In other words, the infusion pump 100 rapidly compresses the infusion tube to achieve the effect of rapid infusion. As shown in FIG. 3, when the rinsing operation is performed, the controller 120 may control the infusion pump 100 to perform the infusion operation. As a result, the liquid flows into the liquid container 500 through the third tube joint 330 of the tube joint structure 300. The liquid in the liquid container 500 may be recycled and reused without wasting the liquid medicine. Referring to FIG. 5, when the rinsing operation is performed, the pressure value first rises from the second pressure value and gradually stabilizes during the rinsing operation. For example, the pressure value may be about 1200, which is slightly lower than the pressure of the liquid when the infusion operation is started at operation S400.

Operation S480 is performed to detect whether there are bubbles in the liquid. For example, the controller 120 may utilize the bubble sensor 140 of the infusion pump 100 to detect whether there are bubbles in the liquid. If there are no bubbles in the liquid, operation S490 is performed. If there are bubbles in the liquid, operation S470 is returned to perform a rinsing operation.

Operation S490 is performed to generate a prompt signal for removing the liquid container 500 and opening the second tube body 220. For example, the controller 120 may generate the prompt signal at this time and display the prompt signal on the display screen 110. After the prompt signal is generated, the effect of removing the liquid container 500 and opening the second tube body 220 may be achieved by the user's manual operation or by machine automatically, but the present disclosure is not limited thereto. For example, as shown in FIG. 1, opening the second tube body 220 may be achieved by releasing the clamping device 400 to allow the liquid to flow through the first tube body 210 and the second tube body 220, thereby delivering the liquid to the patient's body.

After operation S490, the infusion pump 100 may continuously infuse the liquid for a period of time and then the infusion operation is stopped, in which the length of time may be decided by the user, e.g., a doctor or a nursing staff, to determine the amount of liquid medicine needed by the patient.

In summary, the disclosure provides the infusion tube assembly, the infusion device, and the infusion method. By using the infusion structure and method, the bubbles in the infusion tube may be effectively removed with a simple. The removal of the bubbles may be performed without taking out the infusion tube. Furthermore, since the liquid container is connected to the tube joint structure, the loss of the liquid medicine can be reduced during the removal of the bubbles. In addition to reducing the loss of the liquid medicine, the liquid medicine flowing into the liquid container may be recycled and reused.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. An infusion method applied to an infusion pump connected to an infusion tube assembly, wherein the infusion tube assembly comprises a first tube body, a tube joint structure connected to the first tube body, and a second tube body connected to the tube joint structure, the infusion method comprising:
   instructing the infusion pump to perform an infusion operation;
   instructing the infusion pump to stop the infusion operation and generating a bubble alarm when bubbles in a liquid delivered in the infusion tube assembly are detected;
   determining whether a pressure of the liquid drops to a first pressure value after the infusion pump stops the infusion operation;
   further determining whether the pressure of the liquid rises to a second pressure value if the pressure of the liquid drops to the first pressure value; and
   performing a rinsing operation if the pressure of the liquid rises to the second pressure value.

2. The infusion method of claim 1, further comprising:
   before determining whether the pressure of the liquid drops to the first pressure value, generating a prompt signal for clamping the second tube body.

3. The infusion method of claim 1, further comprising:
   before determining whether the pressure of the liquid rises to the second pressure value, generating a first prompt signal for installing a liquid container at the tube joint structure.

4. The infusion method of claim 3, further comprising:
   after no bubbles are detected during the rinsing operation, generating a second prompt signal for removing the liquid container and opening the second tube body.

5. The infusion method of claim 1, further comprising:
   determining whether the bubbles are detected while the rinsing operation is performed; and
   if no bubbles are detected during the rinsing operation, instructing the infusion pump to continuously perform the infusion operation for a predetermined period of time and then stop the infusion operation.

* * * * *